(12) United States Patent
Shamir et al.

(10) Patent No.: US 7,746,469 B2
(45) Date of Patent: Jun. 29, 2010

(54) METHOD FOR PARTICLE SIZE AND CONCENTRATION MEASUREMENT

(75) Inventors: Joseph Shamir, Haifa (IL); Nir Karasikov, Haifa (IL)

(73) Assignee: P.M.L-Particles Monitoring Technologies, Ltd., Emek Ha Yarden (IL)

( * ) Notice: Subject to any disclaimer, the term of this patent is extended or adjusted under 35 U.S.C. 154(b) by 824 days.

(21) Appl. No.: 10/563,662

(22) PCT Filed: Jul. 8, 2004

(86) PCT No.: PCT/IL2004/000616

§ 371 (c)(1),
(2), (4) Date: Jan. 24, 2007

(87) PCT Pub. No.: WO2005/005965

PCT Pub. Date: Jan. 20, 2005

(65) Prior Publication Data

US 2008/0037004 A1    Feb. 14, 2008

(30) Foreign Application Priority Data

Jul. 9, 2003    (IL) .................................. 156856

(51) Int. Cl.
*G01N 21/00*    (2006.01)
(52) U.S. Cl. ...................... 356/338; 356/335
(58) Field of Classification Search ......... 356/335–343, 356/364, 369, 367, 28, 317–318; 250/574, 250/222.2, 225, 304
See application file for complete search history.

(56) References Cited

U.S. PATENT DOCUMENTS

| | | | | |
|---|---|---|---|---|
| 4,806,774 A | * | 2/1989 | Lin et al. | 250/550 |
| 5,063,301 A | * | 11/1991 | Turkevich et al. | 250/574 |
| 5,471,298 A | | 11/1995 | Moriya | |
| 5,999,256 A | | 12/1999 | Jones et al. | |
| 6,084,671 A | * | 7/2000 | Holcomb | 356/511 |

OTHER PUBLICATIONS

Jones, A.R., "Light scattering for particle characterization," Progress in Energy and Combustion Science, Feb. 1, 1999, pp. 1-53.
Piestun Rafael, "Multidimensional Synthesis of Light Fields," Optics & Photonics News, Nov. 2001, p. 28, XP002302678.

(Continued)

*Primary Examiner*—Gregory J Toatley, Jr.
*Assistant Examiner*—Tri T Ton
(74) *Attorney, Agent, or Firm*—Kenyon & Kenyon LLP

(57) ABSTRACT

The present invention provides a system and method of particle size and concentration measurement based on providing a focused, synthesized, non-Gaussian laser beam, causing the beam to interact with the particles, measuring the interaction signal and the number of interactions per unit time of the beam with the particles, and using algorithms to map the interaction signals to the particle size and the number of interactions per unit time to the concentration. The particles are fluid borne, airborne, or on a surface and have a size ranging from sub-micron to thousands of microns. In an embodiment of the invention, the focused, synthesized, non-Gaussian laser beam is a dark beam. The measurements can be made using the duration of interaction with a scanning beam, including dark field.

34 Claims, 13 Drawing Sheets

OTHER PUBLICATIONS

Matizen, Y. et al., "Formation of non-Gaussian light beams with the aid of a spatially inhomogeneous amplitude filter," Soviet Journal of Quantum Electronics, 17 (1987) Jul., No. 7, New York, New York, USA, XP-000709131.

Friedmann Michael et al., "Surface Analysis Using Multiple Coherent Beams," Electrical and Electronics Engineers in Israel, Nov. 5, 1996, pp. 537-540, XP002302680.

Friedmann Michael et al., "Resolution enhancement by extrapolation of the optically measured spectrum of surface profiles," Applied Optics, Jan. 10, 1996; No. 23; XP002302680.

Piestun Rafael et al., "Pattern generation with an extended focal depth," Applied Optics, Aug. 10, 1998, vol. 37, No. 23, XP002302681.

Spektor Boris et al., "Dark beams with a constant notch," Optic Letters, Online!, Dec. 12, 1995, vol. 21, No. 7, pp. 456-458, XP002302682.

T. Allen, "Particle size analysis 1981," John Wiley & Sons, ISBN: 0471262218, Jun. 1983.

B. Weiner et al., "Improvements in Accuracy and Speed Using the Time-of-Transition Method and Dynamic Image Analysis for Particle Size," 1998 American Chemical Society, Ch. 8, pp. 88-102.

R. Piestun et al., "Synthesis of Three-Dimensional Light Fields and Applications," Proc. IEEE, vol. 90(2), pp. 220-244 (Feb. 2002).

R. Piestun et al., "Control of wave-front propagation with diffractive elements," Optical Society of America, vol. 19, pp. 771-773, (1994).

R. Piestun et al., "Unconventional light distributions in three-dimensional domains," Journal of Modern Optics, vol. 43, pp. 1495-1507, (1996).

R. Piestun et al., "Wave fields in three dimensions: analysis and synthesis," Optical Society of America, vol. 13, pp. 1837-1848, (1996).

F. Durst, et al., "Light Scattering by Small Particles Refined Numerical Computations," Report SFB 80/TM/195, Jul. 1981.

* cited by examiner

METHOD FOR PARTICLE SIZE AND CONCENTRATION MEASUREMENT

FIELD OF THE INVENTION

The present invention is related to the field of measuring particle size and concentration. More specifically it relates to the use of optical methods for measuring particle size and concentration. The particles could be liquid borne, airborne or on a surface.

BACKGROUND OF THE INVENTION

Publications and other reference materials referred to herein are incorporated herein by reference in their entirety and are numerically referenced in the following text and respectively grouped in the appended Bibliography, which immediately precedes the claims.

Many techniques exist for particle size and concentration analysis (PSA), they can be reviewed for reference in the book by Terry Alan (1) "Introduction to Particle Size Analysis". The most commonly used techniques are optical, based on the interaction of the measured particles with laser radiation. Especially when approaching the particle size range around 1 micron and below, most of these techniques suffer from inaccuracies due to the effect of the real and imaginary part of the particle's refractive index. It is known, for example, that in some techniques, such as techniques based on Fraunhoffer diffraction analysis, light absorbing particles would be over sized due to energy loss resulting from the absorption, while in high concentration, particles would be under sized due to secondary scattering etc.

An optical technique that is less sensitive to these problems is known as Time of Transition or TOT. In this technique the interaction of a scanning, focused laser beam and the particles is analyzed in the time domain rather than in the intensity domain, resulting in lower sensitivity to variation in the refractive index. A detailed description of the technique appears in the paper (2) by Bruce Weiner, Walter Tscharnuter, and Nir Karasikov. To a great extent, in this technique, a de-convolution algorithm, of the known laser beam profile, from the interaction signal, derives the size. The concentration is derived from the number of interactions per unit time within the known volume of the focused laser beam.

The interaction of the particles in the TOT technique is with a focused scanning laser beam. In order to measure smaller particles, a smaller focused spot should be used. However according to diffraction laws for a Gaussian laser beam, if the beam's waist is D, the divergence of the beam is proportional to $\lambda/D$ where $\lambda$ is the laser's wavelength. The trade-off between the ability to resolve small particles, to the focus volume and the accuracy in measuring concentration is obvious. Thus if the TOT technique is targeted to resolve and measure particles in the micron and sub-micron range it would be limited in its ability to measure low concentrations as the instantaneous focus volume is small and the interaction rate of particles is low. On the other hand, taking a larger spot will improve the concentration measurement rate but will degrade the quality and resolution of the size analysis.

An improvement could be achieved by using a shorter wavelength. This could have a limited effect of, as high as, a factor of 2 only, since going to too short a wavelength will result in absorption of the laser light by the optics and, in the case of particles in liquid, also absorption by the liquid.

It is therefore the purpose of the present invention to introduce a new technique and means to decouple between the two contradicting requirements: the ability to resolve small particles and the ability to measure low concentration using measurements based on single particle interactions.

Further purposes and advantages of this invention will appear as the description proceeds.

SUMMARY OF THE INVENTION

The present invention is a novel method for particle size and concentration analysis. The technique is applicable for liquid borne particles; airborne particles and particles on a surface. The particle size range that can be measured with the method of the invention is from sub-micron to thousands of microns. The ability to decouple focus dimensions from the depth of focus is used for PSA, offering a high resolution and better concentration sensitivity at low concentrations. A special embodiment of the invention addresses the implementation for ultra high concentration.

Provisions for an adaptive range, for triggering "legal" interactions and for the detection of smaller particles in dark field mode are also a part of the present invention.

The method of the invention is based on synthetic beam generation, which can give a factor 15 of improvement over the diffraction limit case in the level of concentration that could be measured for a known size range. By implementing this method, fine particles can be analyzed for size and their concentration can be measured even at very low concentration levels.

The limitation as described hereinabove in the background results from the inherent Gaussian beam profile of the laser beam. Other energy distributions could be synthetically generated. One specific reference, which describes the technique, is reference (3). This publication deals with the generation of three-dimensional light structures used in the invention. It describes the philosophy and the techniques used and it also provides some examples. In particular, the dark beam described is of primary interest for the present invention. Other relevant references are (4)-(9). The dark beam is a laser beam that has a dark spot or line at the center of a beam with an otherwise typically Gaussian envelop. The main advantage of this beam for the purpose of the present invention originates form the fact that the dark central spot/line is narrower than a classical Gaussian spot leading to the possibility of higher sensitivity to the position and structure of an obstructing object. Dark beams can be generated by converting a conventional laser beam with the help of an optical element (usually a diffractive element) or by a special design of the laser resonator in such a way that it emits a dark beam. These laser modes are usually members of a set called Gauss-Laguere and Gauss-Hermit modes.

Dark beams can be generated in such a way that they maintain a sharply defined energy distribution over a wider depth of field, thus offering a better trade-off between size and concentration when implemented in scanning laser probe measuring technique. Further, additional information, unavailable in a TOT is available with the dark beam, enabling more precise measurements. A few ways to realize these forms could be considered and are covered in the references listed in the bibliography.

The use of such beams for PSA is part of the present invention where:

The beam is adapted in focal spot size, dark section and depth of focus to the size and concentration range.

The detection of the scattered light is based on the energy profile extracting the size and concentration information in the most efficient way.

Provisions for overcoming ambiguous measurements in high concentration are also an inherent part of the invention.

Another aspect of the invention is the use of the scanning dark beam technique, described in the present invention, to measure particles in very high concentrations.

The present invention provides a method for particle size and concentration measurement comprising the following steps:
provding a focused, synthesized, non-Gaussian laser beam:
causing the beam to interact with the particles;
measuring the interaction signal and number of interactions per unit time of the beam with the particles; and
using algorithms to map the interaction signals to the particle size and the number of interactions per unit time to the concentration.

According to a preferred embodiment of the invention, the particle size is determined by mapping the interaction pulse width and shape to the size. In another embodiment, the particle size is determined by analyzing the pulse width and shape of the light scattered from said particle when specially polarized light is used for structured illumination. According to another embodiment, the particle size is determined by differential interference of the light scattered from the particle with the two lobes of a line singularity synthesized, non-Gaussian laser beam.

The particles can be suspended in a fluid, airborne, or on a surface and their size can range from sub-micron to thousands of microns. The focal properties of the laser beam are changed depending on the size and concentration range of the particles.

The focused, synthesized, non-Gaussian laser beam can be a dark beam and the measurements are made in the intensity domain or by using the scanning technique. The synthesized, non-Gaussian laser beam can be circular, rectangular, or linear.

According to one method of the invention, the non-Gaussian beam can be generated by employing a mask over a Gaussian laser beam. The Gaussian beam is spatially modulated by use of, for example, a spatial-filter, a set of spatial filters, an electronic spatial light modulator, or a liquid crystal device. The spatial modulation can comprise intensity modulation, alternating intensity modulation, polarization modulation, phase modulation and combinations of these. The modulation can be implemented either statically or dynamically.

In preferred embodiments of the invention, the non-Gaussian beam is generated by directly modifying the laser cavity or combining the beams from several lasers.

The interaction of the focused beam with the particles is accomplished either by causing the particles to flow relative to a stationary beam or by providing a scanning mechanism that provides a linear or a rotary scanning path for the focused beam.

In a preferred embodiment of the invention, a detection system is used to measure radiation scattered at 90 degrees to the beam direction to verify single particle interaction in the focal area or to measure additional dark field information. This detection system can, for example, comprise a CCD camera, one or more avalanche photodiodes, or any set of other detection devices or combination thereof.

In another embodiment of the invention, a detection system is used to measure radiation scattered at 90 degrees to the beam direction in order to detect smaller particles using dark field measurement.

In another embodiment of the invention, high concentrations of particles are measured by using a reflection mode, collecting the back-scattered interaction energy from the particle. These measurements can be carried out using the set up and algorithm of the present invention.

In another embodiment of the invention the particle size is determined in a transmission mode where the forward scattered light from said particle interferes with the synthesized, non-Gaussian laser beam thus achieving increased sensitivity in transmission mode.

The invention comprises also the use of one or several detection systems that are connected in various ways, such as addition, differential, coincidence.

According to the method of the invention, the algorithms used to map the interaction signals to the particle size and the number of interactions per unit time to the concentration can be either explicitly based on the interaction signals or based on an advanced artificial intelligence machine, such as a Neural Network or support vector machine (SVM).

The present invention further provides a system for particle size and concentration measurement comprising:
one or more lasers to provide a Gaussian laser beam;
a scanning mechanism;
means for converting the Gaussian laser beam into a structured (non-Gaussian) laser beam; and
detection means using one or several detection systems, connected in various ways, such as addition, differential, coincidence.

In a preferred embodiment of the invention, the means for converting the Gaussian laser beam into a structured (non-Gaussian) laser beam consist of a combination of a spatial filter and a lens.

In other preferred embodiments, the system of the invention additionally comprises a second detection system to measure the radiation scattered at 90 degrees to the beam direction. The system can comprise also a beam splitter to divert back-scattered interaction energy from the particle to the detector.

According to preferred embodiments of the invention, the synthesized, non-Gaussian laser beam can be circular or linear.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

The invention deals with a novel way for particle size and concentration measurement using a laser beam whose energy profile is optimized for the particle's size and concentration range.

A preferred embodiment of the invention involves the use of a dark beam, i.e. a beam with a dark spot/line in its center. This beam profile in combination with the enhanced depth of focus, which is another feature of the invention, allows operation in lower concentrations and for smaller particles. Additional data, which exists as both broadening of the main beam and change of the central dark spot, yields information on the particle size. The dynamic range of measurement is thus extended where smaller particles interact with the dark spot/line whereas larger particles interact with the main beam.

One aspect of the field known as singular optics, that is the subject of a great deal of theoretical and practical study, is the subject of dark beams. One group of these singular beams comprises optical vortices, which to a large extent resemble vortices in fluids. For example they have angular momentum that behaves according to the regular physical conservation laws and therefore it is possible to destroy the optical vortex only by the application of an opposite angular momentum. Since this doesn't happen during the normal propagation of the beam, the vortex will be preserved even when the beam undergoes physical changes of size such as, for example, when it is focused. If the focusing lens transmits a singular beam, it will continue to be singular as long as it propagates.

When any beam of light crosses the interface between two media (for example air and glass) the boundary conditions require that the division of the intensity of the beam on both sides of the boundary has a similar form although the absolute intensity on both sides will be different because of reflection and scattering. This also applies to singular beams. Therefore they will continue to propagate as singular beams in the second medium. It should be noted that if the boundary is not of high quality, than the crossing can distort the shape of the beam and can cause light to be scattered into the singular region but cannot destroy the singularity itself.

A singular beam can be seriously degraded under conditions of strong random scattering. The degradation is manifested in that the dark center of the beam fills with light. This degradation results in a reduction of the signal to noise ratio and in this way places restraints on the concentration of particles that can be measured using techniques based on use of this type of beam. This problem is also encountered in other methods and is no worse than in methods based on scanning with a Gaussian beam. Because the signal measured by the method of the invention has a very special character, it appears that the limit on the concentration will be much higher than that using prior art methods of concentration and size measurement.

Figure 1:
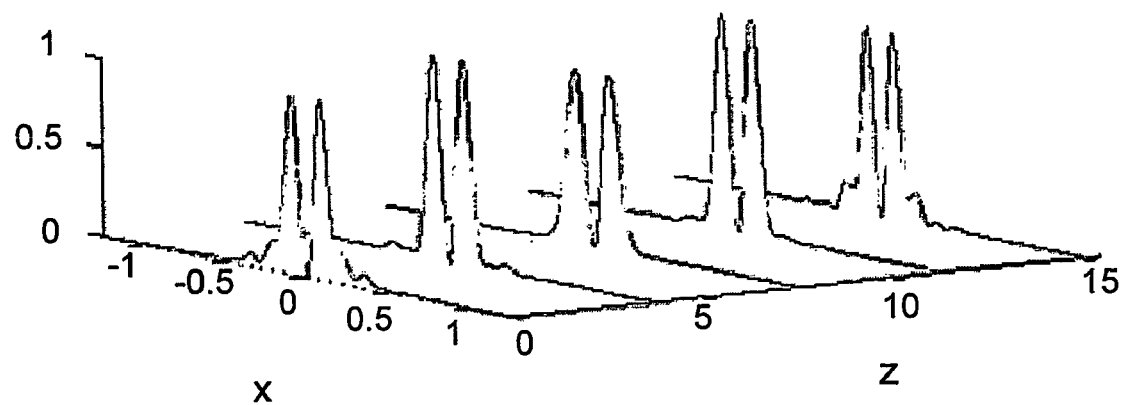
FIG. 1 schematically shows an example of a simulation of a dark beam.

The dark beam is effectively a Gaussian beam modulated such that there is an additional central zero of ~20% of the width of the waist. For a 1 micron Gaussian beam this zero has an effective width of typically 0.2 micron. An example of a simulation of the above beam is shown in FIG. 1. In the figure, the vertical (y) axis represents the intensity in arbitrary units, the x-axis the beam width in microns, and the z-axis distance in the direction of propagation of the beam measured in mm. It is clear from the simulation results that the depth of focus far exceeds that of a conventional Gaussian beam.

The detection considerations for a dark beam are similar to the detection with a conventional Gaussian beam, but with the following advantages:

There is an additional information due to the convolution information of the Zero in the beam;

Effectively there is a higher resolution as convolution information is generated with an effective kernel waist of 0.2 micron; and The detection is dark field, as in the central zone there would be energy only from the scattered light. This yields higher sensitivity at smaller particle size.

As a result of these differences from a conventional Gaussian beam, the detection of smaller particles and a wider concentration range is facilitated. The interaction signals for small and for large particles are described hereinbelow and show that small particles mostly affect the depth of the dark spot whereas large particles react with the wider beam on a classical convolution concept. Since the convolution resolution is determined by the kernel, it is clear that the dark beam approach of the invention offers measurement of 5 times smaller particles compared to the conventional Gaussian approach without affecting the upper range of particle size that can be measured.

Figure 2:
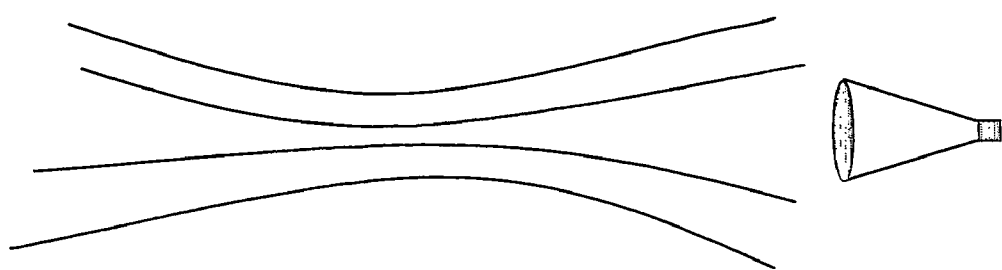
FIG. 2 schematically shows a possible beam geometry.
Figure 3:
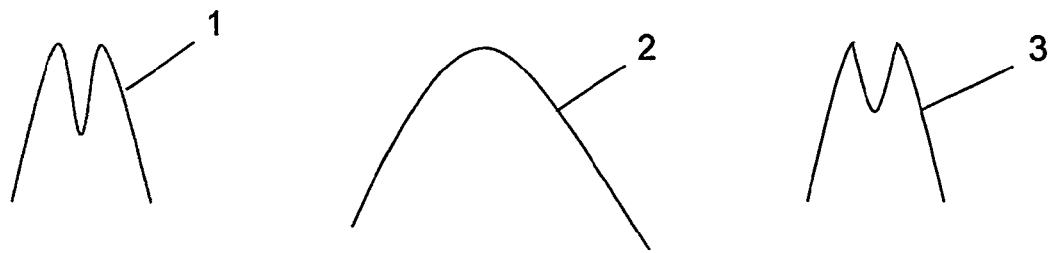
FIG. 3 schematically shows the signal profile and its shape obtained by interaction with particles of different size.

The beam geometry is shown schematically in FIG. 2. FIG. 3 illustrates the mechanism. Viewing the light intensity scattered by a very small particle crossing a dark beam with the spatial profile (1), the detection system will register a similar pattern in the time domain. However, the interaction signal obtained for a large particle (2) is characterized by the elimination of the dark center and by broadening of the signal. The interaction with an intermediate sized particle (3) maintains the original signal width but decreases the depth of the dark spot. There are thus two major parameters of the signals for measurement—the signal width and the depth of the central dip. The two signal parameters are sensitive in complementary size ranges and hence assist in broadening the measurement range. The beam design of the present invention applies to both beam width and the shape of the dark spot/line, as well as to the depth of field. There are thus advantages in measured size range and in measured concentration range.

It is seen that when interacting with a particle larger than the beam, the major effect is beam broadening and the disappearance of the central dip; when interacting with a particle smaller than the beam, the main effect is the decrease of the depth of the signal dip. Thus the single beam provides two signal parameters for better coverage of the size range. As the synthesized beam is typically not Gaussian, the algorithm for de-convolving the spot is not straightforward and, among other approaches; one based on artificial intelligence is proposed—training the system with several mono-dispersed samples.

Three basic approaches are employed in the invention to generate the non-Gaussian beams:

1. a hybrid technique employing a mask over a laser Gaussian beam;
2. generating the dark beam within the laser resonator; and
3. creating a fully synthetic beam profile.

Figure 4:
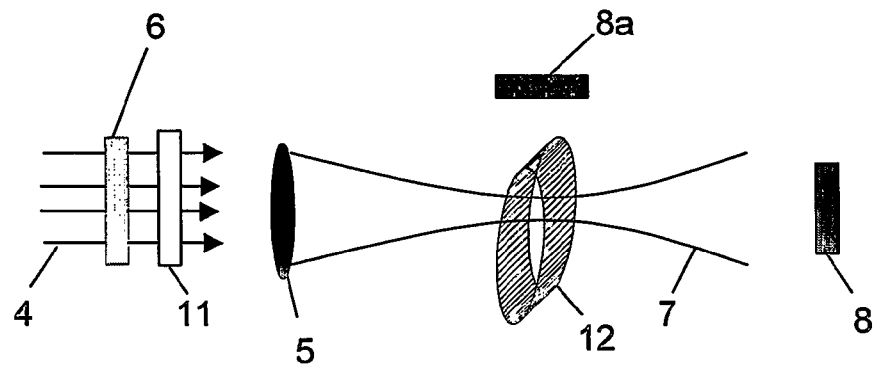
FIG. 4 schematically shows a possible embodiment layout of the invention.

The hybrid technique is schematically shown in FIG. 4. There are several procedures available to construct optical systems, which convert a Gaussian laser beam (4) into a structured beam (7). FIG. 4 depicts one possible embodiment of the invention, where the scanning mechanism (11) is placed between spatial-filter (6) and lens (5). As will be realized by experienced persons, the configuration shown in FIG. 4 is a schematic representation of one of many possible implementations of the optical system of the invention. Another embodiment of the invention employs a liquid crystal device to accomplish the spatial modulation. The interaction of the laser beam with the particles is accomplished either by causing the particles to flow relative to a fixed beam or by scanning the beam over the particles. The scanning mechanism (11) facilitates either a rotary scanning path (12) or a linear path. It can be realized by many solutions including a wedge prism, an acousto-optic deflector, etc. Examples of light structures that can be used are Bessel beams and singular beams of various orders, either in one dimension or two dimensions. In FIG. 4 the structured beam (7) interacts with the particles in the focal zone of the beam. Detection system (8) detects the interaction signal.

The detection of "legal particles", intercepting the beam in its focal region, becomes more challenging with the enhanced beam profile of the present invention. Obscuration by multiple particles along the extended focus could erroneously be interpreted as a single particle. The invention optionally addresses this by using an additional detection system, which is the triggering detection system. Referring again to FIG. 4, the detector assembly (8a) is used for the validation of the particles in the focal zone. This detection system detects the scattered radiation at typically 90 degrees to the beam direction and functions as verification to a single particle interaction in the focal area and/or as an additional dark field signal. Only when the detection system (8a) verifies a single particle in the measuring zone, is the signal at detection system (8) analyzed for size. The field of view of this side detection system can be changed so that it matches the focal region. An array detector such as a CCD camera can be used as well.

Figure 5:
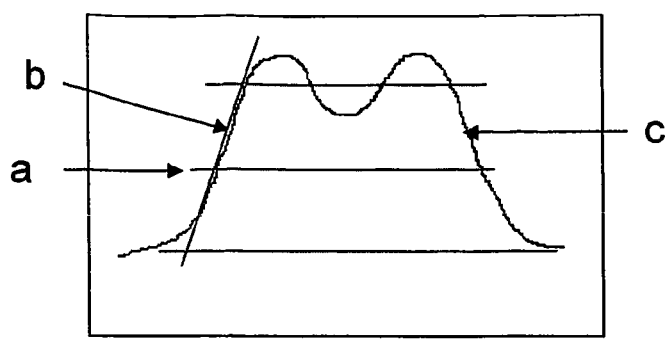
FIG. 5 shows schematically the signal that is detected by the detection system when a Gaussian laser beam scans a round, symmetric, partially transparent particle.

The interaction signal is the convolution of the light beam and the particle. FIG. 5 shows schematically the signal that is detected by detection system (8) and/or (8a) (FIG. 4) when a Gaussian laser beam scans a round, symmetric, partially transparent particle. A particle of this type could be, for instance, a drop of crude oil in water. In FIG. 5, the vertical axis represents intensity and the horizontal axis the time domain signal width. Line "a" is the line that represents 50% of the particle width and lines "b" and "c" the rise and fall times of the signal respectively.

The above FIG. 5 is an illustration for an interaction of a Gaussian beam with a particle in transmission mode (forward scattering). For the structured beam the interaction is more complex, nevertheless there is a clear pattern differentiating between particles interacting in or out of the focal zone. The analysis program scans the particles and rejects illegal particles, i.e. particles that are only partly present in the measurement volume, which is only in the focal region of the laser. The particles that are found to be legal are included in the statistical distribution and in the calculation of the concentration.

The velocity of the interaction of the laser beam with the particles is determined first. The sampling time is derived from the scanning speed and the sampling frequency to achieve the required scanning resolution. When a legal particle is detected, the size of each particle is calculated at typically 50% of the particle width by multiplying the number of samples by the sampling time. In order to speed up the measurement time, a look up table showing the relationship between the number of samples and the size of the particle in microns is prepared at the beginning of the measurements. An alternative approach is using Artificial Intelligence to map interaction signals to size, using first a known set of calibration materials.

Whereas the detection is typically performed in bright field, forward detection, by detection system (8), in some cases of smaller particles, the side detection system (8a) could be used for the sizing. This is a dark field measurement. The advantage of using the dark field is in an enhanced signal to noise ratio and as such, better resolution of smaller particles.

It should be noted that special consideration must be given to particles whose size is equal to, or smaller than, the spot size of the laser. For the larger particles the contribution of the laser spot size is less dominant than for particles whose size is approximately equal to the spot size. The addition of dark beam measurements to those of the bright field yields two signals that supplement each other.

Figure 6:
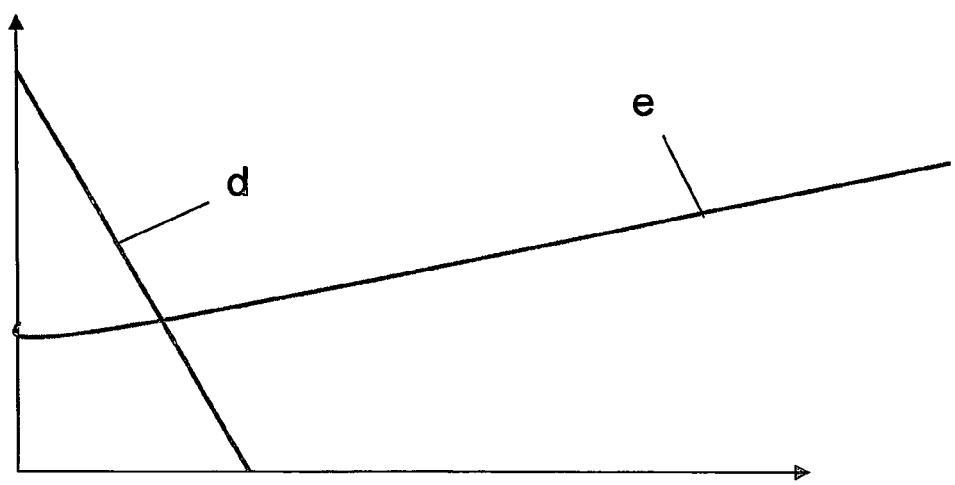
FIG. 6 shows schematically the relationship between intensity and the width of the interaction signal and the depth of the modulation.

FIG. 6 shows schematically the relationship, using normalized intensity, between both the width of the interaction signal and the depth of the modulation (vertical axis) and the particle size (horizontal axis). The line labeled "e" is the width of the interaction signal as shown by numeral 2 in FIG. 3. Line "d" is the depth of the modulation of the dark beam for small particles represented by numeral 3 in FIG. 3.

Figure 7:
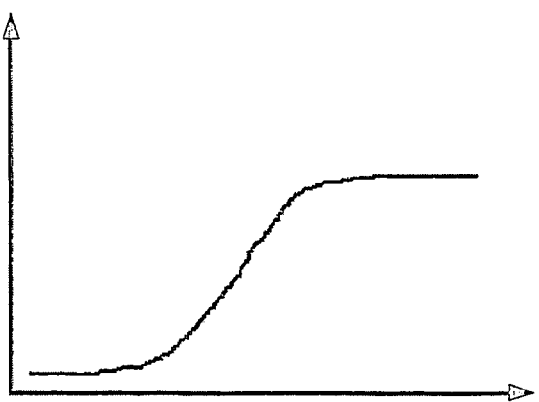
FIG. 7 shows schematically the relationship between the intensity and particle size.

FIG. 7 shows schematically the relationship between the intensity of interaction (vertical axis) and particle size (horizontal axis). From FIG. 7, it can be seen that the intensity of small particles is low because they only partially block the beam falling on the detection system. On the other hand, large particles block more of the detection system and the intensity increases. The straight horizontal part on the right of the graph is for particles that are very large (approximately 10 times the spot size).

The signals detected at the detection system (8) are as described previously in reference to FIG. 3 for a specific reference embodiment. It should be noted that the bright field detection system should have a dynamic range wide enough to withstand the "no particle" bright field signal.

In other embodiments of the invention, the modulation of the Gaussian beam is, in addition to intensity modulation and phase modulation that are constant in time, alternating modulation, polarization modulation, wavelength modulation or combinations of these.

The Fourier transform representing the energy distribution in the focus could thus be designed for optimal distribution and depth of focus. Configurations with and without the dark spot/line, described in FIG. 3, could be realized.

As mentioned hereinabove, a fully synthetic beam profile is an alternative to the hybrid technique described above. In using this technique, specific beam profiles are generated by directly modifying the laser cavity or by combining the beams from several lasers. Scalar beam structuring as well as vector (polarization) assisted structuring can be used.

Other embodiments of the invention are concerned with beam optimization where, for different size ranges, a different spatial filter (6) (FIG. 4) is used to generate a different beam profile. This offers the optimal choice of size resolution and concentration accuracy. The variable spatial filter (6) could be in the form of a set of filters that are mechanically mounted in front of the focusing lens. Another possible embodiment is fully electronic, with a spatial light modulator (SLM) that can be used as an electronically controlled spatial filter.

In another embodiment of the invention, the measured size range of the particles is increased by simultaneously generating two or more different beam profiles in the focal zones, where each beam profile is for a different wavelength. In a preferred variation of this embodiment three different wavelengths—red, green, and blue—are used.

There are other possible embodiments using the dark field detection, which are also part of the present invention. Blocking the zero order forward scattered energy before the detection system (8) is an example for such a possible embodiment.

In some cases the stable concentration to be measured is very high, causing enhanced light scattering and multiple scattering. Typical examples are Liposomes with concentration of 10 exp 13 1/cc; emulsions with concentrations of 10 exp 9 particles/cc, etc. In these cases the light beam is diffused after just a short path in the sample. The invention addresses this, in the manner schematically shown in FIG. 8, by minimization of the optical path using a thin cell and, more importantly, by using a reflection/back scatter mode. In this mode the focusing lens (5) is used also to collect the back-scattered interaction energy from the particle (10). The back-scattered energy is diverted via a beam splitter (9) to the detection system (8b). Designing the focal zone of interaction to be very close to the sample boundary, minimizes the optical path in the scattering media and therefore the multiple scattering, thus enabling operation in high concentration.

The measuring procedure of the invention comprises several steps. Experienced persons will recognize that each of these steps can be realized in a number of different ways and will be able to optimize the procedure for a particular situation. The following is a list of the steps of the procedure, including illustrative but not limitative examples of some of the options that are available for carrying them out:

A laser source having the required power and wavelength is selected. For very small particles, i.e. <0.5 micron, a shorter wavelength would be preferred, typically Ar 488 nm or similarly green or blue diodes. For larger particles a HeNe laser at 632.8 nm or a semiconductor laser in the visible or near IR could be used.

A beam profile is generated with the required energy distribution and depth of field in accordance to the size and concentration ranges.

A scanning mechanism for the beam is introduced. The scanning could be acousto-optic deflection; a rotating wedge prism; a rotating, inclined, optical flat; a rotating polygon; or other means of scanning. The scanning velocity should be >10 times the particle velocity in case of a rotary scan and >5 times the particles velocity in case of a linear scan. The beam can be swept back and forth through the sampling area, scanned linearly and unidirectionally, or caused to rotate about the optical axis tracing out a circle on a plane passing through the focal region and perpendicular to the propagation direction.

Figure 8:
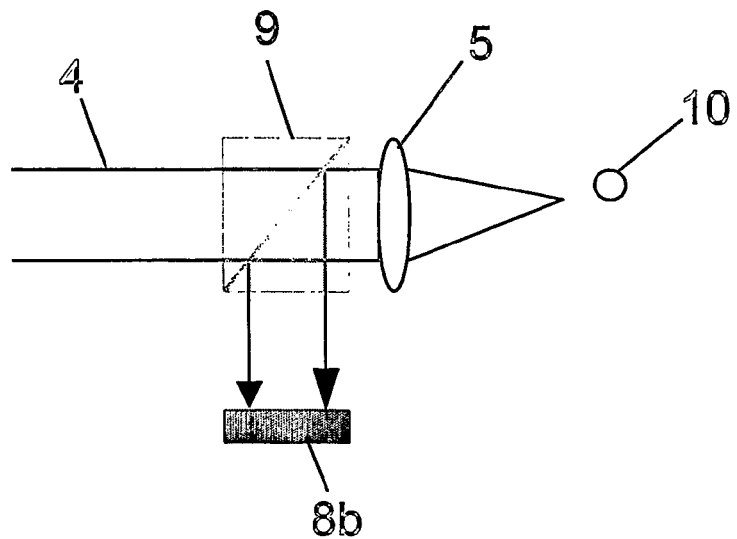
FIG. 8 schematically shows layout of the embodiment of the invention used at high concentration.
Figure 18:
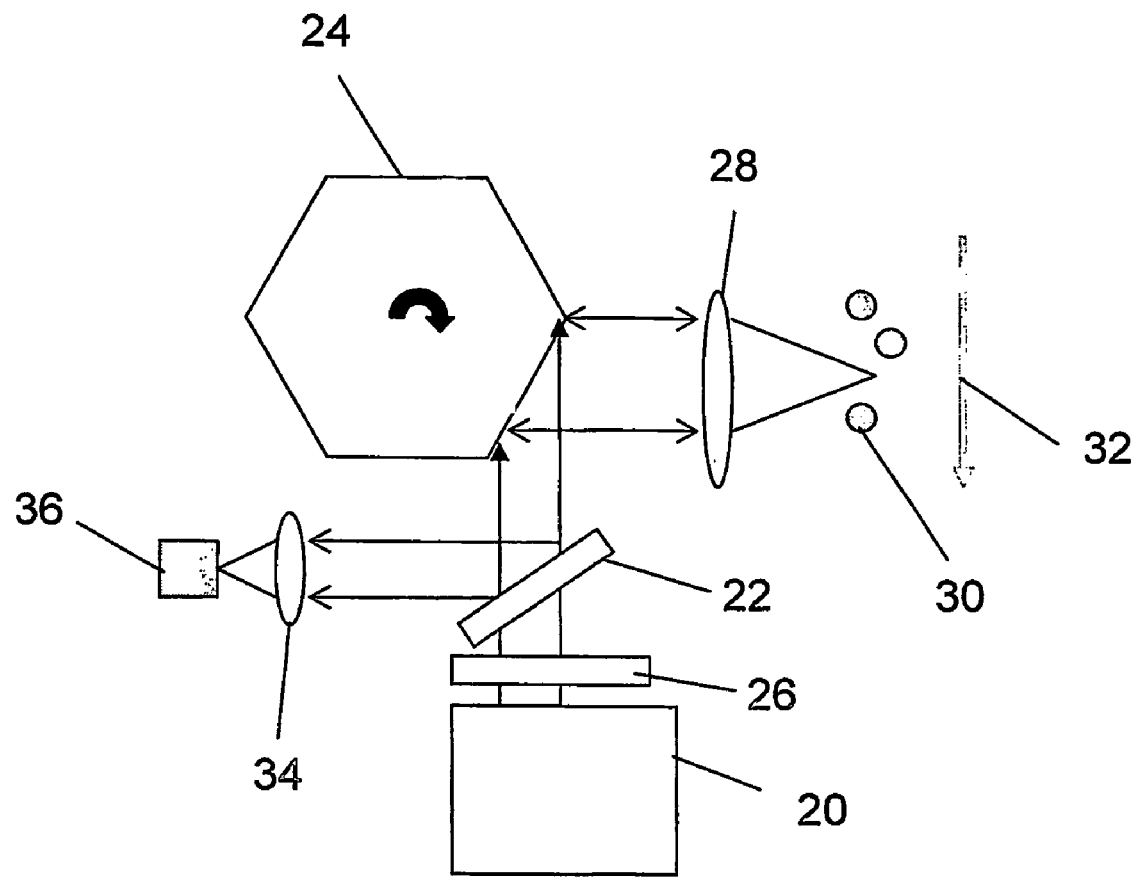
FIG. 18 schematically shows an exemplary optical set-up and detection scheme for making the measurements using back scattered light.

An optical set-up is constructed. The basic optical set-up for detecting forward scattering is shown in FIG. 4, with a detection system for the bright field and a detection system for the dark field. FIG. 8 shows one embodiment and the basic arrangement for detection of back scattering. FIG. 18 shows in more detail an exemplary optical set-up and detection scheme for making the measurements using back scattered light. In FIG. 18, light from laser source 20 passes through spatial filter 26, which converts it into a non-Gaussian structured beam, and then through beam splitter 22. It then impinges on the facets of revolving polygon scanner 24. The laser beam that is reflected off the facets of scanner 24 passes through focusing lens 28 and is linearly scanned across particles 30 flowing in the direction indicated by arrow 32. The laser light that is backscattered by the interaction with particles 30 returns through lens 28, is reflected by scanner 24 and beam splitter 22, and is collected by lens 34 onto the detection system 36.

The bandwidth of the detection system should be >2Vspot/Rmin, where Vspot is the scanning laser velocity in the interaction area and Rmin is the smallest particle to be detected. The sensitivity of the detection system should comply with the expected signals in the proper scattering direction corresponding to the specific embodiment. Scattering calculations can be found in the book written by Durst, reference (10).

The detected signals are fed via a digitizing card to a computer for analysis. Digitization rate should be typically $2\pi$ times the bandwidth.

The signal analysis is conducted according to the method described with reference to FIGS. 3, 6 and 7. A mapping of interaction signal to size is thus realized.

The number of interactions per unit time is calibrated either by building a look-up table interpolating between known concentrations measured or explicitly by calculating the instantaneous volume and the total volume covered in a unit time in order to determine the concentration.

Algorithms for mapping signal to size and interaction rate to concentration can be explicitly based on interaction signals as in FIG. 3, or based on an advanced artificial intelligence machine such as Neural Network or SVM (support vector machine).

Figure 19:
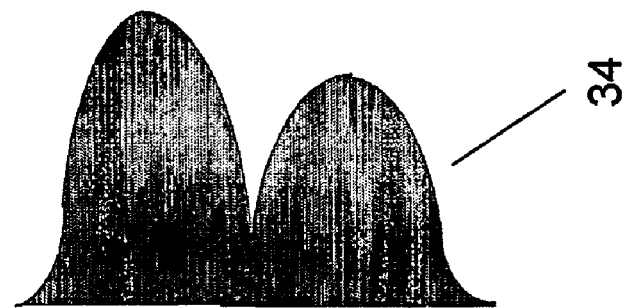
FIG. 19 schematically illustrates the principle of the forward scattering interference method.
Figure 19:
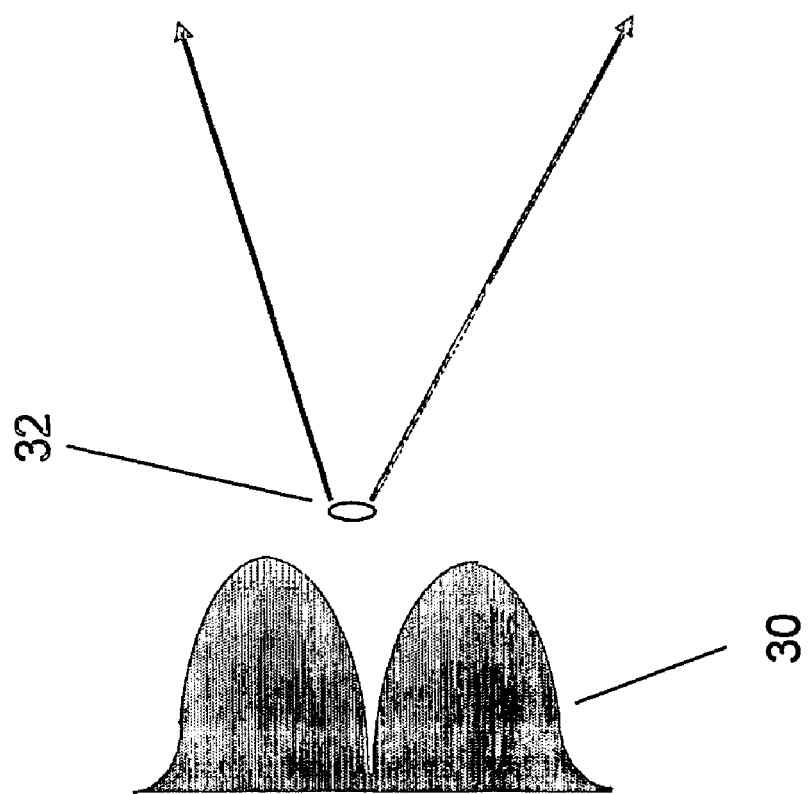

In addition to the measurement and detection schemes described herein, there exists an embodiment of the invention, which increases the signal in forward scattering. This method, known as interference method, is used in forward scattering of a linear dark beam (see hereinbelow) and is useful for measuring particles that are much smaller than the beam size. The method is based on the fact that a small particle illuminated by a light beam scatters a small fraction of the beam and the scattered wave will interfere with the original beam. If the original beam is Gaussian, then it is not affected significantly by the presence of the particle. If, however, the beam is a linear dark beam, then due to the opposite phase of the two lobes on each side of the singularity, a large differential signal will be measured between the two lobes of the output signal. The effect is shown in FIG. 19. The incoming dark beam 30 is symmetric before it encounters particle 32. The light scattered from particle 32 interferes constructively with the upper lobe and destructively with the lower lobe to yield output signal 34. The differences between the two lobes of signal 34 can be analyzed to yield information about the size of particle 32.

The following examples are provided merely to illustrate the invention and are not intended to limit the scope of the invention in any manner.

EXAMPLES

A. Beam Synthesis

Both circular (doughnut) and linear (slit) dark beams have been synthesized and their measured energy distributions compared with the theoretical analysis.

Figure 9A:
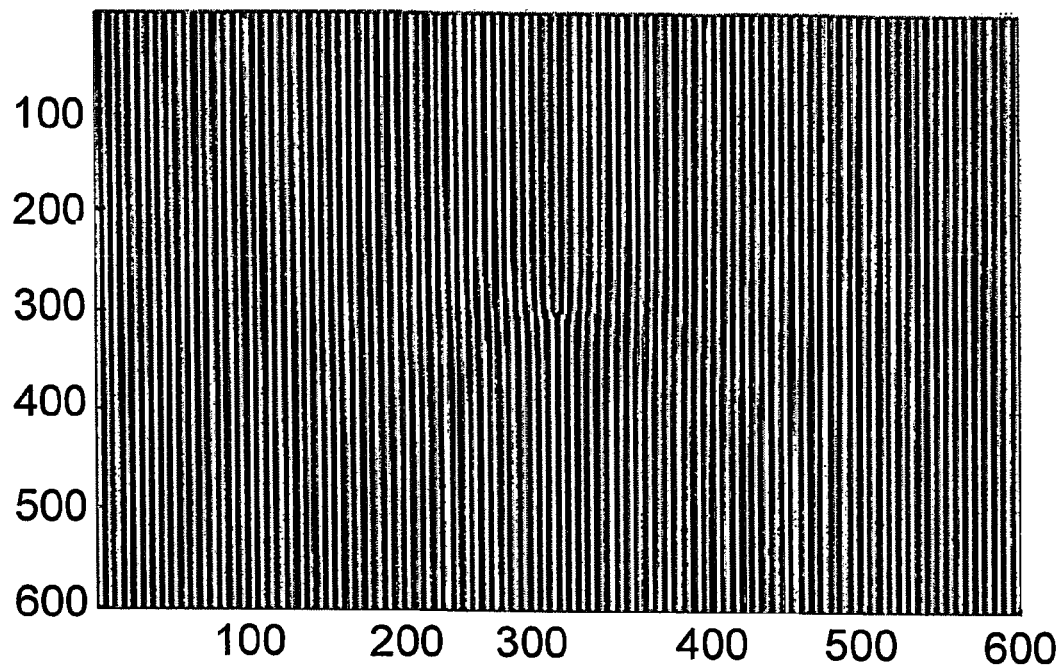
FIG. 9A shows the pattern used to realize a circular dark beam.
Figure 9B:
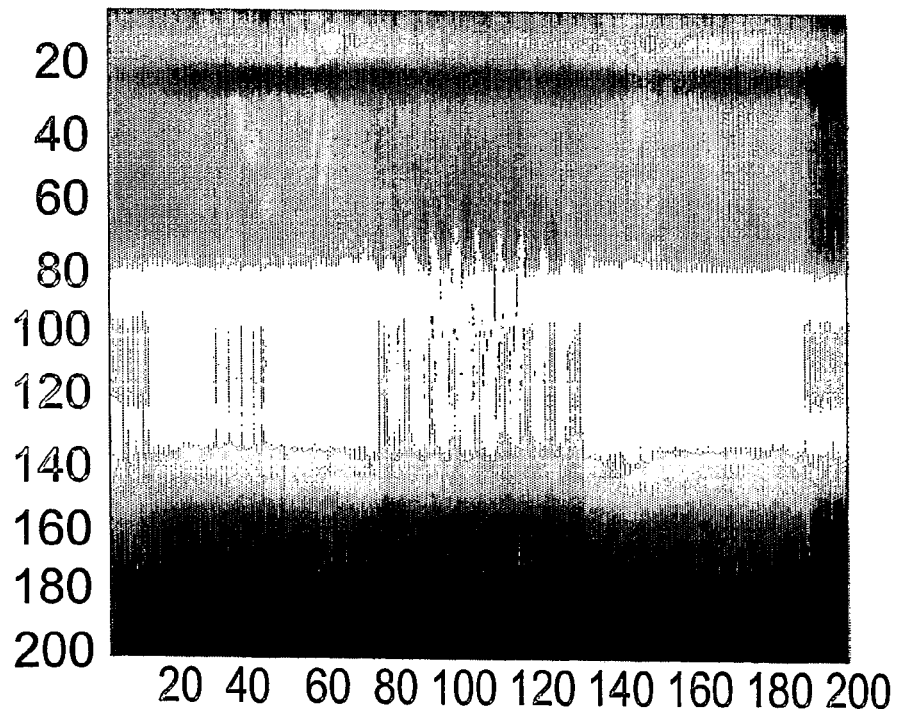
FIG. 9B shows the pattern of FIG. 9A illuminated with a Gaussian beam.
Figure 10:
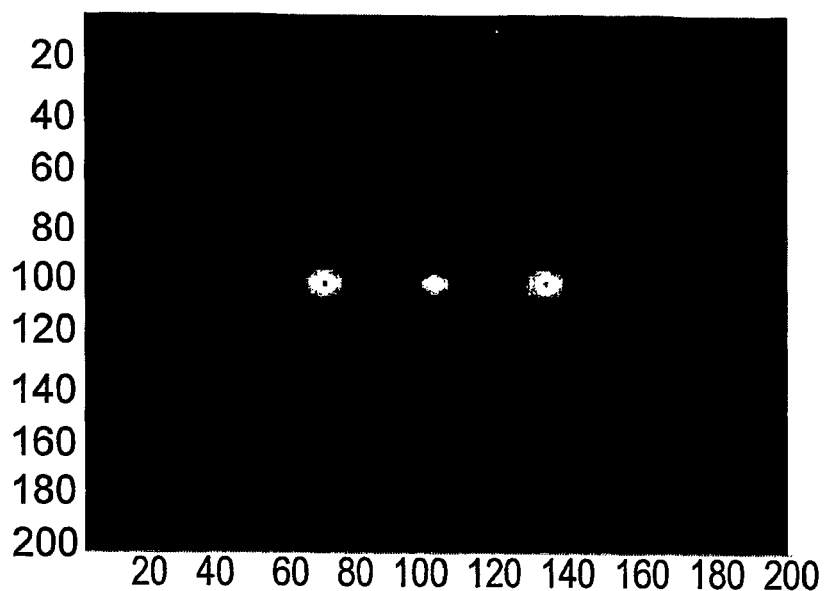
FIG. 10 is a photograph of the far field image showing the zero and first order of the energy pattern.
Figure 11:
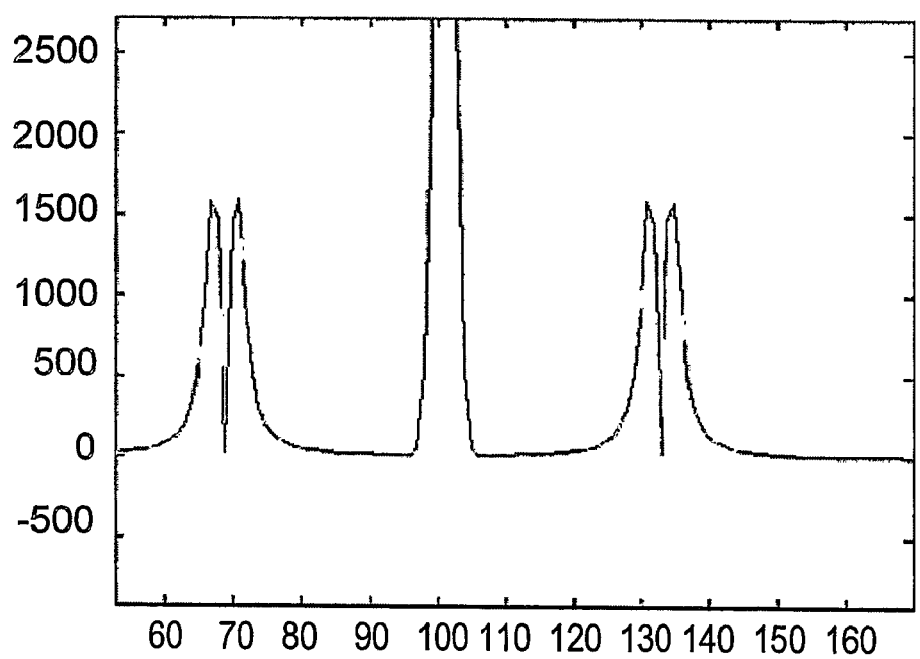
FIG. 11 shows the corresponding energy distribution.

FIG. 9A shows one possible pattern used to realize the circular dark beam. FIG. 9B shows the pattern of FIG. 9A illuminated with a Gaussian beam (a HeNe laser). FIG. 10 is a photograph of the far field image showing the zero and first order of the energy pattern. FIG. 11 shows the corresponding energy distribution.

Figure 12:
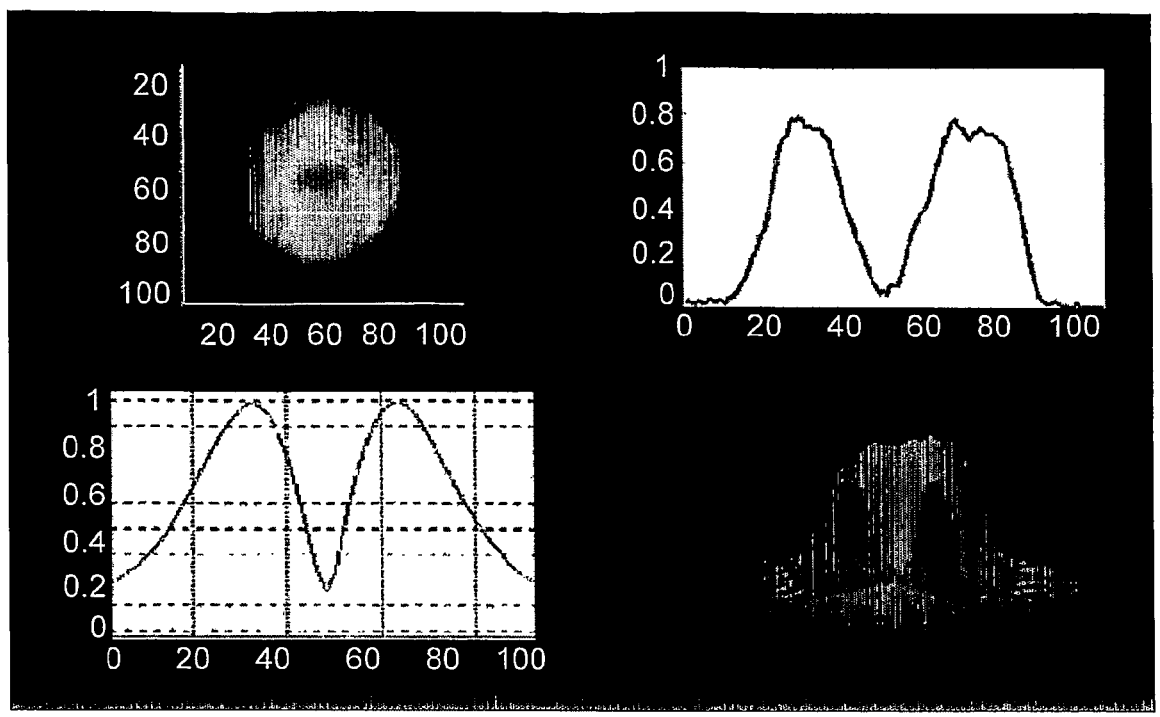
FIG. 12 shows a comparison of the experimental results to the simulation for the circular beam shown in FIG. 10.

FIG. 12 shows a comparison of the experimental results to the simulation for the circular beam shown in FIG. 10. The image on the left side of FIG. 12 is the simulation and the image on the right side of FIG. 12 shows the experimental results. In the two graphs, the vertical axis represents the relative intensity and distance in pixels is measured along the horizontal axis.

Figure 13A:
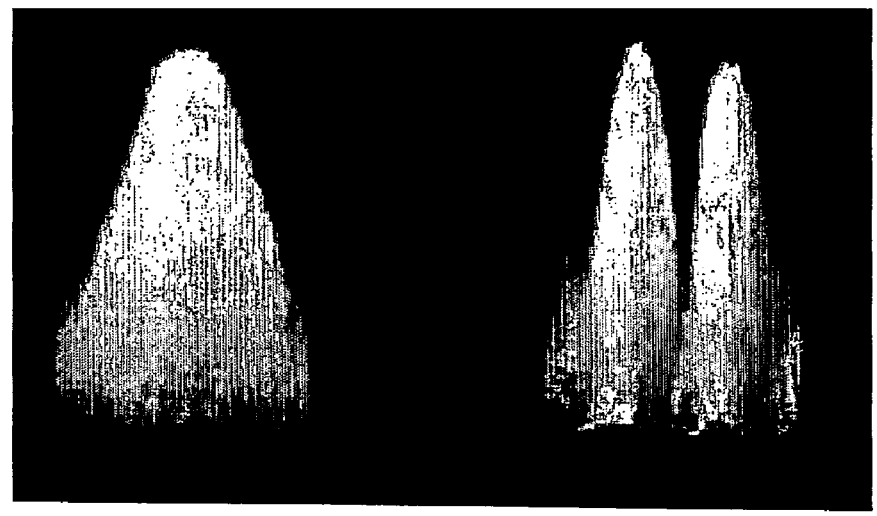
FIGS. 13A and 13B show the experimental results for the zero and first order energy distributions of a slit beam.
Figure 13B:
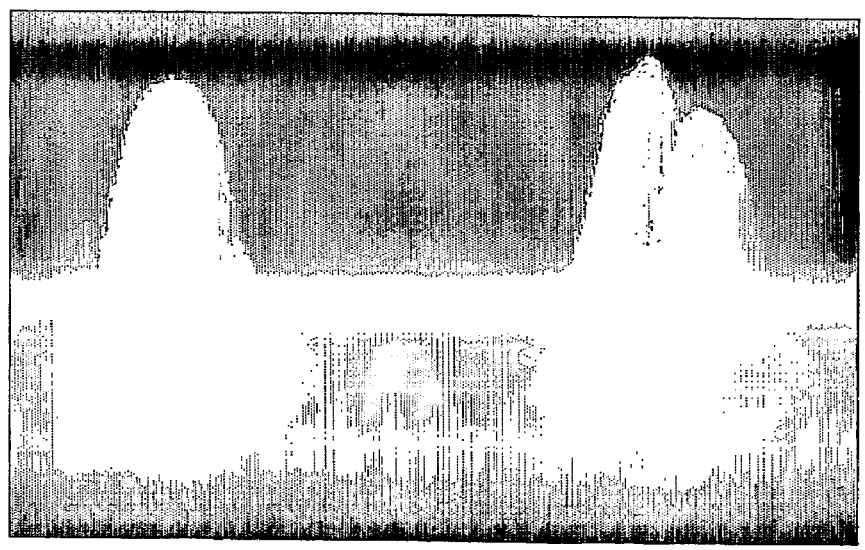
Figure 14A:
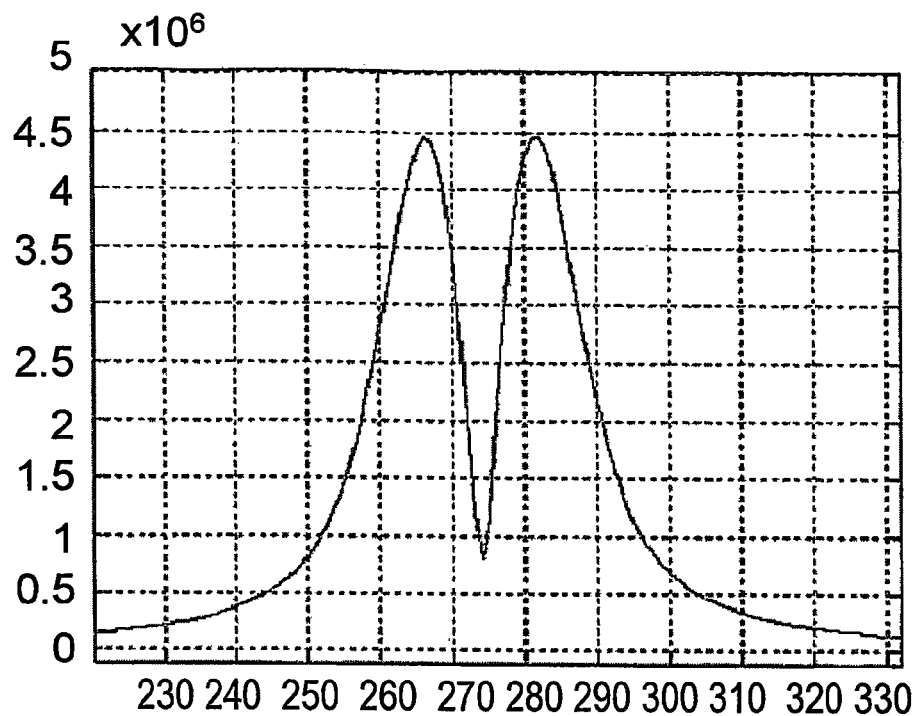
FIGS. 14A to 14E are simulations showing respectively the convolution between the circular beam and the backscatter from particles having diameters of 0.1, 0.2, 0.4, 1, and 2 microns.
Figure 14B:
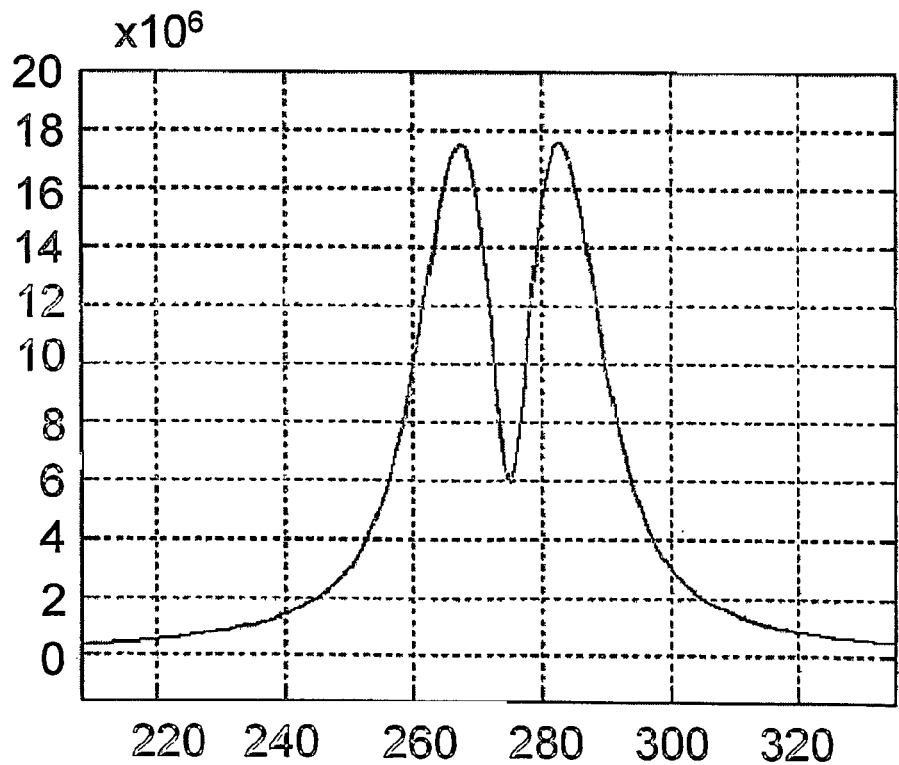
Figure 14C:
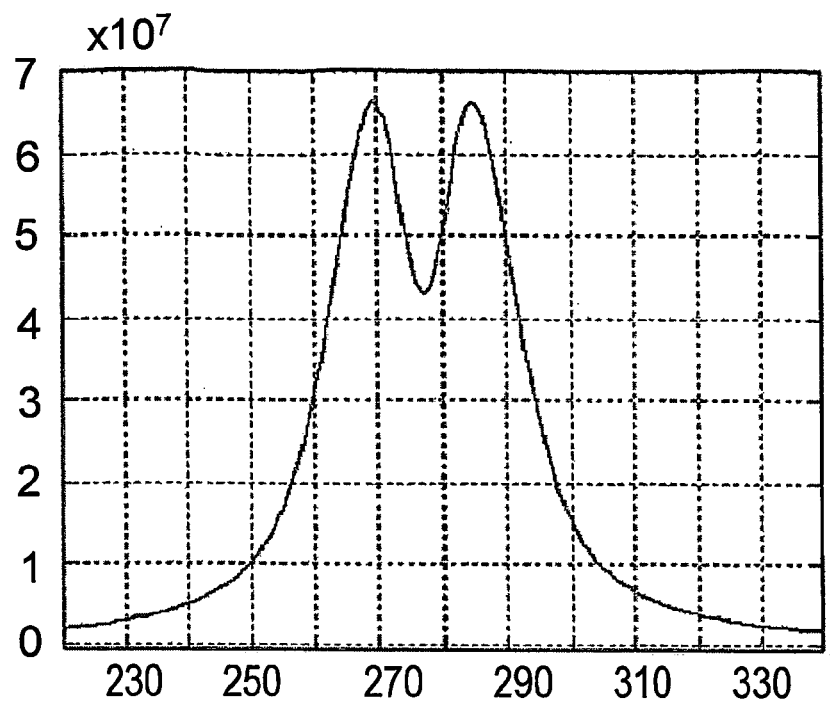
Figure 14D:
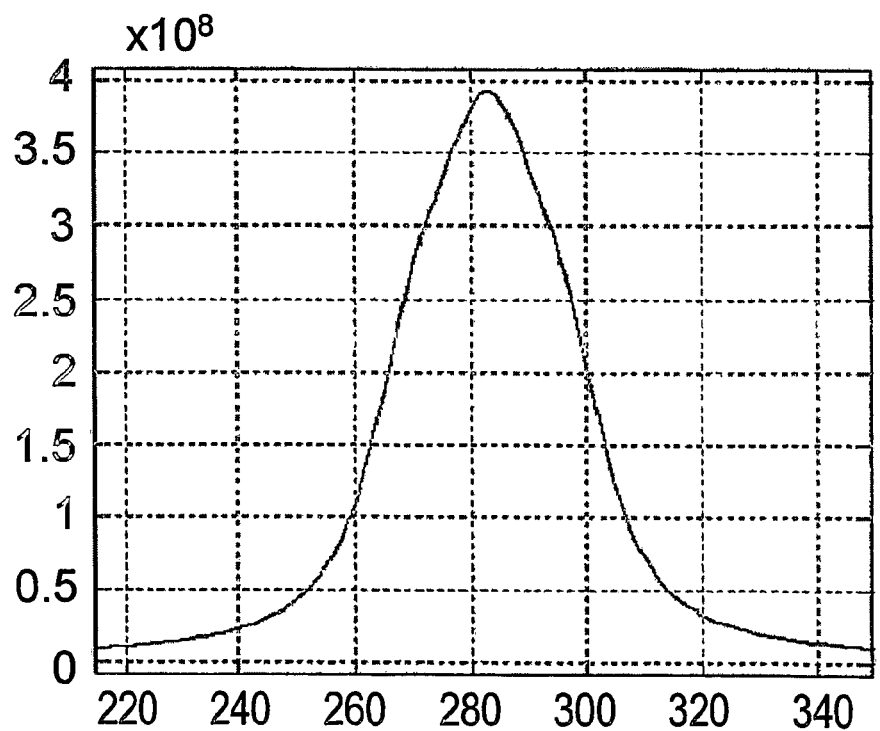
Figure 14E:
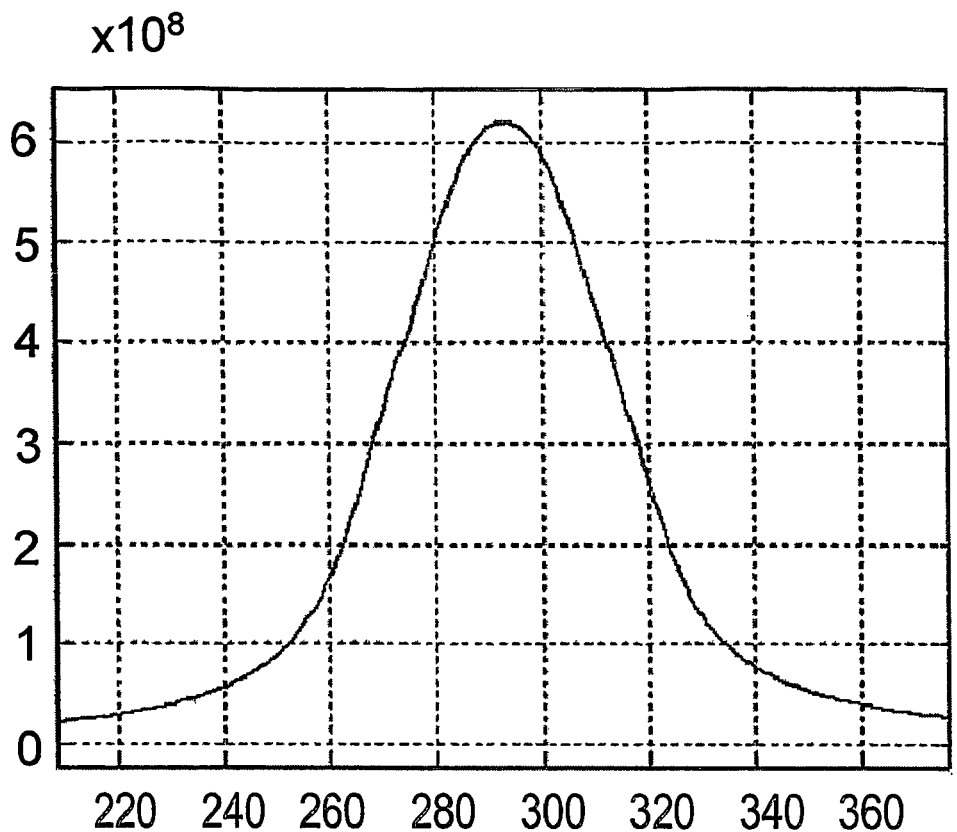

A linear dark beam is generated by using a spatial light filter that has a phase shift of Π on half of its plane. The experimental results for the zero and first order energy distributions of the slit beam are shown in FIGS. 13A and 13B.

B. Detection Simulations

A scanning laser beam was used to make the interaction between the particles and the laser beam. A detection system transfers the signals to an acquisition board on which the signal is analyzed and the size distribution of the particles is constructed. The algorithm for analyzing the particle size is divided into two methods: a dark beam for small particles (typically 0.1-1 microns) and a regular Gaussian beam for larger particles. The backscatter from the particles with a synthesized circular beam, having an outside diameter of 3 microns and inside diameter of 0.45 microns at 1/e, was used in the simulations.

FIGS. 14A to 14E show the results of the simulations showing respectively the backscatter interaction simulation between the circular beam and the particles having diameters of 0.1, 0.2, 0.4, 1, and 2 microns.

The results of the simulations are shown in the following table in which the columns show the size of the particles, the maximum, minimum, and ratio of the intensities and the width of the signal at half maximum of the intensity.

| SIZE | MAX | MIN | MIN/MAX | WIDTH |
| --- | --- | --- | --- | --- |
| 0.1 | 4.5 | 0.7 | 0.1556 | 32 |
| 0.2 | 18 | 6 | 0.3333 | 32 |
| 0.4 | 66 | 43 | 0.6515 | 33 |
| 1 | 400 | 400 | 1 | 33 |
| 2 | 620 | 620 | 1 | 40 |

Figure 15:
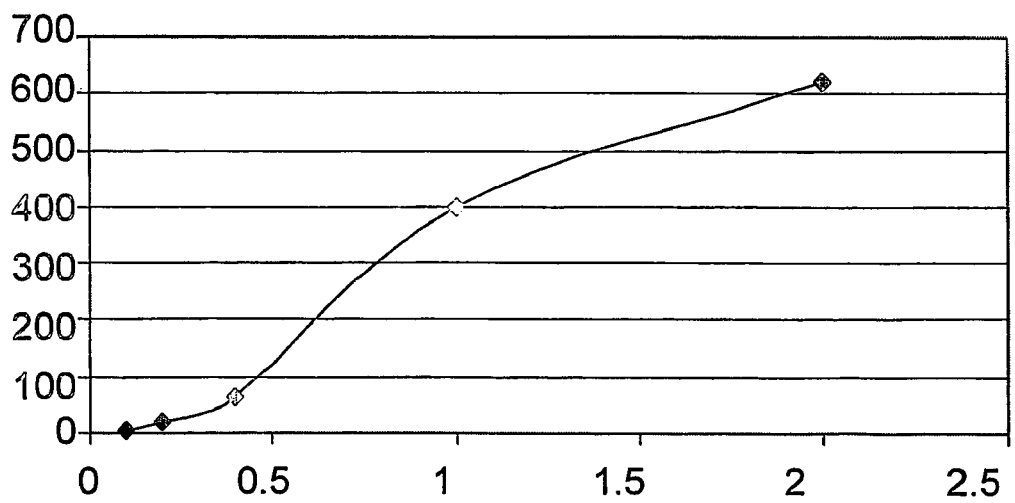
FIGS. 15, 16, and 17 are simulations showing respectively the maximum signal, width at half intensity, and ratio of the minimum to the maximum intensity as functions of the particle size.
Figure 16:
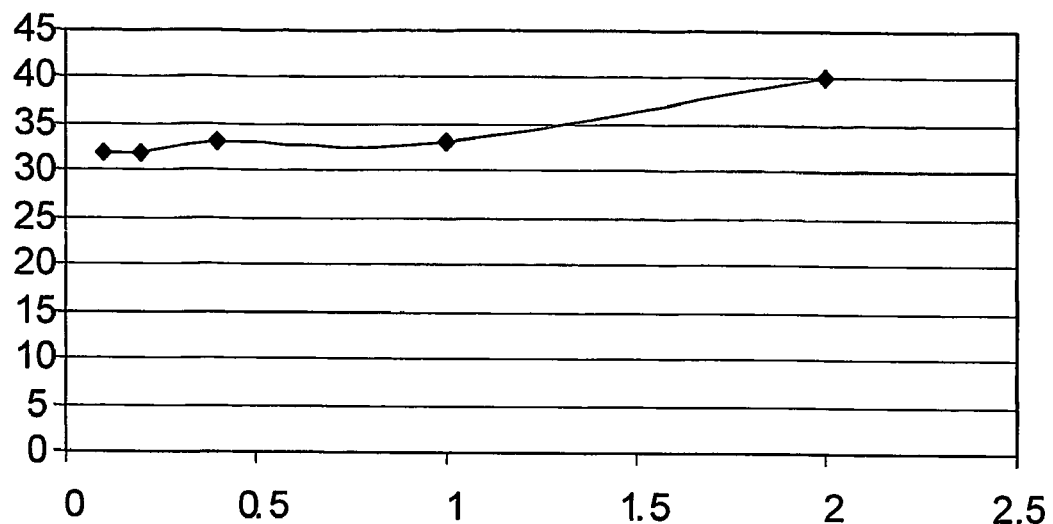
Figure 17:
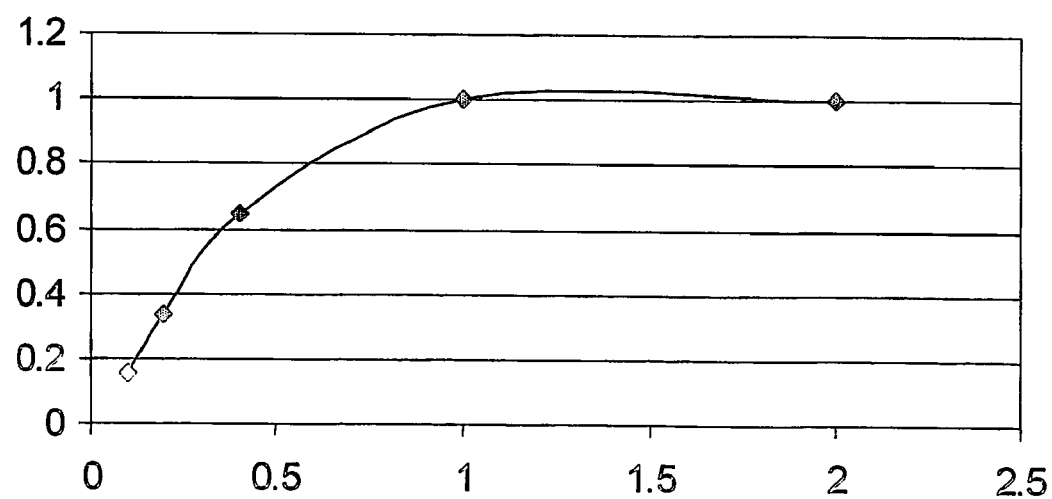

FIGS. 15, 16, and 17 are the results of the simulations showing respectively the maximum signal, width at half intensity, and ration of the minimum to the maximum intensity as functions of the particle size in microns.

The method of the present invention is applicable to measuring, for example:
- airborne powders dust/pollution;
- particles suspended in liquid, such as polymer beads;
- high concentration emulsions, such as mayonnaise; and
- Particles spread on a microscope slide.

Although embodiments of the invention have been described by way of illustration, it will be understood that the invention may be carried out with many variations, modifications, and adaptations, without departing from its spirit or exceeding the scope of the claims.

BIBLIOGRAPHY

1. T. Allen, Particle size analysis John Wiley & Sons; ISBN: 0471262218; June, 1983.
2. W. Tscharnuter, B. Weiner and N. Karasikov, TOT theory.
3. R. Piestun, and J. Shamir, "Synthesis of three-dimensional light-fields and applications" Proc. IEEE, Vol. 90(2), 220-244, (2002).
4. R. Piestun, and J. Shamir, "Control of wavefront propagation with diffractive elements," Opt. Lett., Vol. 19, pp. 771-773, (1994).
5. B. Spektor, R. Piestun and J. Shamir, "Dark beams with a constant notch," Opt. Lett., Vol. 21, pp. 456-458, 911 (1996).
6. R. Piestun, B. Spektor and J. Shamir, "Unconventional Light Distributions in 3-D domains," J. Mod. Opt., Vol. 43, pp. 1495-1507, (1996).
7. R. Piestun, B. Spektor and J. Shamir, "Wave fields in three dimensions: Analysis and synthesis," J. Opt. Soc. Am. A, Vol. 13, pp. 1837-1848, (1996).
8. M. Friedmann and J. Shamir, "Resolution enhancement by extrapolation of the optically measured spectrum of surface profiles," Appl. Opt. Vol. 36, pp. 1747-1751, (1997).
9. R. Piestun, B. Spektor and J. Shamir, "Pattern generation with extended focal depth," Appl. Opt., Vol. 37, pp. 5394-5398, (1998).
10. F. Durst, M. Macagno, G. Richter, "Light scattering by small particles, a refined numerical calculations". Report SFB 80/TM/195 July 1981.

The invention claimed is:

1. A method of particle size and concentration measurement comprising the following steps:
   using one or more lasers to produce a Gaussian laser beam;
   using means for converting said Gaussian laser beam into a focused, synthesized, non-Gaussian dark beam;
   causing said particles to flow relative to a stationary dark beam or using a scanning mechanism to cause said beam to interact with said particles;
   using a detection system to measure the interaction signal and number of interactions per unit time of said dark beam with said particles; and
   feeding an output of said detection system into a computer comprising algorithms adapted to map said interaction signals to said particle size and said number of interactions per unit time to said concentration.

2. A method according to claim 1, wherein the particles are one of fluid borne, airborne, and on a surface.

3. A method according to claim 1, wherein the size of the particles ranges from sub-micron to thousands of microns.

4. A method according to claim 1, wherein the measurements are made in the intensity domain.

5. A method according to claim 1, wherein the measurements are made using the mapping of the interaction pulse width to particle size.

6. A method according to claim 1, wherein the focal properties of the laser beam are changed depending on the size and concentration range of the particles.

7. A method according to claim 1, wherein the non-Gaussian beam is generated by employing a mask over a Gaussian laser beam.

8. A method according to claim 1, wherein the Gaussian beam is spatially modulated.

9. A method according to claim 8, wherein the Gaussian beam is one of spatially modulated by use of spatial-filter, a set of spatial filters, an electronic spatial light modulator, and a liquid crystal device.

10. A method according to claim 8, wherein the spatial modulation of the Gaussian beam is chosen from the group comprising:
   (i) intensity modulation;
   (ii) phase modulation;
   (iii) wavelength modulation;
   (iv) polarization modulation; and
   (v) combinations of these.

11. A method according to claim 8, wherein the spatial modulation is implemented statically.

12. A method according to claim 8, wherein the spatial modulation is implemented dynamically.

13. A method according to claim 1, wherein the non-Gaussian beam is generated by one of directly modifying the laser cavity and combining the beams from several lasers.

14. A method according to claim 1, wherein the interaction of the focused beam with the particles is accomplished by providing the scanning mechanism that provides a linear scanning path for said focused beam.

15. A method according to claim 1, wherein the interaction of the focused beam with the particles is accomplished by providing the scanning mechanism that provides a rotary scanning path for said focused beam.

16. A method according to claim 1, further comprising the use of a second detection system to measure radiation scattered at 90 degrees to the beam direction one of (i) to verify single particle interaction in the focal area and (ii) as an additional dark field information.

17. A method according to claim 16, wherein the second detection system used to measure radiation scattered at 90 degrees to the beam direction comprises a CCD camera.

18. A method according to claim 16, wherein the second detection system used to measure radiation scattered at 90 degrees to the beam direction comprises several detectors.

19. A method according to claim 18, wherein the several detectors are connected in a way selected from the group: addition, differential, and coincidence.

20. A method according to claim 1, wherein the detection system is used to measure radiation back-scattered from the particles.

21. A method according to claim 1, further comprising the use of a detector to measure radiation scattered at 90 degrees to the beam direction to detect smaller particles using dark field TOT measurement.

22. A method according to claim 1, wherein high concentrations of particles are measured by using a reflection, back scatter, mode, collecting the back-scattered interaction energy from the particle.

23. A method according to claim 18, wherein counting interaction signals, of the scanning laser beam, per unit time is used to measure high concentrations of particles.

24. A method according to claim 1, wherein the algorithms adapted to map the interaction signals to the particle size and the number of interactions per unit time to the concentration are explicitly based on said interaction signals.

25. A method according to claim 1, wherein the algorithms adapted to map the interaction signals to the particle size and the number of interactions per unit time to the concentration are based on an advanced artificial intelligence method.

26. A method according to claim 25, wherein the advanced artificial intelligence method is a Neural Network or support vector method (SVM).

27. A system for particle size and concentration measurement comprising:
   one or more lasers to provide a Gaussian laser beam;
   a scanning mechanism;
   means for converting said Gaussian laser beam into a focused, synthesized, non-Gaussian laser beam; and
   detection means;
   wherein said focused, synthesized, non-Gaussian laser beam is a dark beam and said means for converting said Gaussian laser beam into said focused, synthesized, non-Gaussian laser beam are chosen from the following group:
   a combination of a spatial filter and a lens; and
   a liquid crystal device.

28. A system according to claim 27 additionally comprising a second detection system to measure the radiation scattered at 90 degrees to the beam direction.

29. A system according to claim 27, additionally comprising a beam splitter to divert back-scattered interaction energy from the particle to the detection means.

30. A method according to claim 1, wherein the synthesized, non-Gaussian laser beam is circular.

31. A method according to claim 1, wherein the synthesized, non-Gaussian laser beam is linear.

32. A method according to claim 1, wherein the particle size is determined by differential interference of the light scattered from said particle with the two lobes of a linear synthesized, non-Gaussian laser beam.

33. A method according to claim 1, wherein the particle size is determined by analyzing the polarization of the light scattered from said particle.

34. A method according to claim 1, wherein two or more confocal beams are simultaneously generated, each of said beams having a different wavelength.

* * * * *